US010514372B2

(12) United States Patent
De Prisco et al.

(10) Patent No.: US 10,514,372 B2
(45) Date of Patent: Dec. 24, 2019

(54) DIGITAL ROCK ANALYSIS SYSTEMS AND METHODS THAT RELIABLY PREDICT A POROSITY-PERMEABILITY TREND

(71) Applicants: Giuseppe De Prisco, Houston, TX (US); Jonas Toelke, Houston, TX (US)

(72) Inventors: Giuseppe De Prisco, Houston, TX (US); Jonas Toelke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 997 days.

(21) Appl. No.: 13/972,772

(22) Filed: Aug. 21, 2013

(65) Prior Publication Data

US 2014/0058676 A1 Feb. 27, 2014

Related U.S. Application Data

(60) Provisional application No. 61/692,541, filed on Aug. 23, 2012.

(51) Int. Cl.
*G01N 33/24* (2006.01)
*G01N 15/08* (2006.01)

(52) U.S. Cl.
CPC ............. *G01N 33/24* (2013.01); *G01N 15/08* (2013.01)

(58) Field of Classification Search
CPC ................................ G01N 15/08; G01N 33/24
See application file for complete search history.

(56) References Cited

U.S. PATENT DOCUMENTS 6,516,080 B1  2/2003 Nur
9,080,946 B2  7/2015 De Prisco et al.
(Continued)

FOREIGN PATENT DOCUMENTS

CN 101556703 10/2009
CN 102426390  4/2012
(Continued)

OTHER PUBLICATIONS

Liu, Jie, et al., "Improved Estimates of Percolation and Anisotropic Permeability from 3-D X-ray Microtomography Using Stochastic Analyses and Visualization", G3: An Electronic Journal of the Earth Sciences, May 29, 2009, Voi. 10, No. 5, AGU and the Geochemical Society.*

(Continued)

*Primary Examiner* — Alexander Satanovsky
*Assistant Examiner* — Mark I Crohn
(74) *Attorney, Agent, or Firm* — Chamberlain Hrdlicka (57) ABSTRACT

The pore structure of rocks and other materials can be determined through microscopy and subjected to digital simulation to determine the properties of fluid flows through the material. To determine a porosity-permeability over an extended range even when working from a small model, some disclosed method embodiments obtain a three-dimensional pore/matrix model of a sample; measure a distribution of porosity-related parameter variation as a function of subvolume size; measure a connectivity-related parameter as a function of subvolume size; derive a reachable porosity range as a function of subvolume size based at least in part on the distribution of porosity-related parameter variation and the connectivity-related parameter; select a subvolume size offering a maximum reachable porosity range; find permeability values associated with the maximum reachable porosity range; and display said permeability values as a function of porosity.

20 Claims, 5 Drawing Sheets

(56) References Cited

U.S. PATENT DOCUMENTS

| | | | |
|---|---|---|---|
| 9,285,301 | B2 | 3/2016 | De Prisco et al. |
| 2009/0288880 | A1 | 11/2009 | Wojcik et al. |
| 2010/0128932 | A1 | 5/2010 | Dvorkin et al. |
| 2010/0135536 | A1* | 6/2010 | Dvorkin ............... G01N 23/046 382/109 |
| 2010/0198638 | A1 | 8/2010 | Deffenbaugh et al. |
| 2011/0004447 | A1 | 1/2011 | Hurley et al. |
| 2011/0181701 | A1 | 7/2011 | Varslot et al. |
| 2012/0179436 | A1 | 7/2012 | Fung |
| 2012/0239361 | A1 | 9/2012 | Vargas-Guzman |
| 2012/0281883 | A1* | 11/2012 | Hurley ............... G01N 21/6458 382/109 |
| 2013/0338976 | A1 | 12/2013 | De Prisco et al. |
| 2014/0019054 | A1 | 1/2014 | De Prisco et al. |

FOREIGN PATENT DOCUMENTS

| | | |
|---|---|---|
| WO | 2013/188239 | 12/2013 |
| WO | 2014/011448 | 1/2014 |
| WO | 2014/031882 | 2/2014 |

OTHER PUBLICATIONS

Eaton, Timothy, "On the importance of geological heterogeneity for flow simulation", Sedimentary Geology 184 (206 187-201.*

Fens, Theo, "Petrophysical Properties from small rock samples using Image Analysis techniques" (Nov. 14, 2000).*

Schlumberger Oilfield Glossary. https://www.glossary.oilfield.slb.com/Terms.aspx?LookIn=term%20name&filter=porosity, retrieved on Aug. 9, 2019. (Year: 2019).*

De Prisco, Giuseppe, et al., "Digital Rock Analysis Systems and Methods with Multiphase Flow REV Determination", U.S. Appl. No. 13/524,758, filed Jun. 15, 2012, 22 pgs.

De Prisco, Giuseppe, et al., "Digital Rock Analysis Systems and Methods with Multiphase Flow REV Determination", PCT Appl. No. PCT/US2013/044773 filed Jun. 7, 2013, 20 pgs.

De Prisco, Giuseppe, et al., "Digital Rock Analysis Systems and Methods with Reliable Multiphase Permeability Determination", U.S. Appl. No. 13/549,354, filed Jul. 13, 2012, 25 pgs.

De Prisco, Giuseppe, et al., "Digital Rock Analysis Systems and Methods with Reliable Multiphase Permeability Determination", PCT Appl. No. PCT/US2013/049113, filed Jul. 9, 2013, 21 pgs.

De Prisco, Giuseppe, "Digital Rock Analysis Systems and Methods that Reliably Predict a Porosity-Permeability Trend", U.S. Appl. No. 61/692,541, filed Aug. 23, 2012, 24 pgs.

Walls, Joel, et al., "Method for Characterizing a Wellbore Depth Interval from Rock Fragments", U.S. Appl. No. 61/845,272, filed Jul. 11, 2013, 7 pgs.

Grader, Abraham S., et al., "Conditioning of Expanded Porosity", U.S. Appl. No. 61/863,508, filed Aug. 8, 2013, 15 pgs.

Adalsteinsson, David, et.al, "Accurate and Efficient Implementation of Pore-Morphology-based Drainage Modeling in Two-dimensional Porous Media", Transport in Porous Media (2006) 65: 337-358.

Hazlett, R. D., "Simulation of Capillary-Dominated Displacements in Microtomographic Images of Reservoir Rocks", Transport in Porous Media 20: 21-35, 1995, Kluwer Academic Publishers, The Netherlands.

Hilpert, Markus, et al., "Pore-Morphology-Based Simulation of Drainage in Totally Wetting Porous Media", Advances in Water Resources 24 (2001) 243-255; Elservier Science Ltd.

Liu, Jie, et al., "Application of percolation theory to microtomography of structured media: Percolation threshold, critical exponents, and upscaling", Physical Review E 83, 016106 (2011), American Physical Society.

Liu, Jie, et al., "Improved Estimates of Percolation and Anisotropic Permeability from 3-D X-ray Microtomography Using Stochastic Analyses and Visualization", G3: An Electronic Journal of the Earth Sciences, May 29, 2009, vol. 10, No. 5, AGU and the Geochemical Society.

Papatzacos, Paul, "Cellular Automaton Model for Fluid Flow in Porous Media", Complex Systems 3 (1989) 383-405, Complex Systems Publications, Inc., Stavanger, Norway.

Hilfer, R., "Transport and Relaxation Phenomena in Porous Media", Advances in Chemical Physics, 1996, pp. 299-424, vol. XCII, John Wiley & Sons, Inc.

Biswal, B., et al., "Three-Dimensional Local Porosity Analysis of Porous Media", Physica A 255 (1998) 221-241, Elsevier Science B.V.

Hilfer, R., "Review on Scale Dependent Characterization of the Microstructure of Porous Media", Transport in Porous Media 46: 373-390, 2002, Kluwer Academic Publishers, The Netherlands.

AU Examination Report No. 1, dated Jun. 15, 2012, Appl No. 2013274604, "Digital Rock Analysis Systems and Methods with Multiphase Flow REV Determination," filed Jun. 7, 2013, 2 pgs.

AU Patent Examination Report, Sep. 7, 2016, Appl No. 2013289017, "Digital Rock Analysis Systems and Methods with Reliable Multiphase Permeability Determination," Filed Jul. 2, 2013, 2 pgs.

AU Patent Examination Report, dated Sep. 29, 2016, Appl No. 2013305672, "Digital Rock Analysis Systems and Methods that Reliably Predict a Porosity-Permeability Trend," Filed Aug. 22, 2013, 3 pgs.

CN Office Action, dated Aug. 3, 2016, Appl No. 2013800511532, "Digital Rock Analysis Systems and Methods that Reliably Predict a Porosity-Permeability Trend," Filed Aug. 23, 2013, 22 pgs.

CN Office Action, dated Jul. 5, 2016, Appl No. 201380031517.0, "Digital Rock Analysis Systems and Methods with Multiphase Flow REV Determination," Filed Jun. 7, 2013, 29 pgs.

EP Search Report, dated Mar. 9, 2016, "Digital Rock Analysis Systems and Methods with Reliable Multiphase Permeability Determination," Appln No. 13817013.9, 8 pgs.

EP Extended Search Report, dated Jan. 12, 2016, "Digital Rock Analysis Systems and Methods with Multiphase Flow REV Determination," Appln No. 13803847, 8 pgs.

GCC Examination Report, dated Jul. 27, 2016, Appl No. 24652, "Digital Rock Analysis Systems and Methods with Multiphase Flow REV Determination," Filed Jun. 15, 2013, 5 pgs.

PCT International Search Report and Written Opinion, dated Jan. 23, 2014, Appl No. PCT/US13/66244, "Digital Rock analysis systems and methods that reliably predict a porosity-permeability trend," filed Aug. 22, 2013, 12 pgs., 12 pgs.

PCT International Search Report and Written Opinion, dated Dec. 19, 2013, Appl No. PCT/US13/049113, "Digital Rock Analysis system and methods with realiable multiphase permeability determination," filed Jul. 2, 2013, 14 pgs.

PCT International Search Report and Written Opinion, dated Nov. 26, 2013, Appl No. PCT/US13/44773, "Digital Rock Analysis Systems and Methods with Multiphase Flow REV Determination," filed Jun. 7, 2013, 27 pgs.

PCT International Preliminary Report on Patentability, dated Mar. 5, 2015, Appl. No. PCT/US2013/056244, "Digital Rock Analysis Systems and Methods that Reliably Predict a Porosity-Permeability Trend," filed Aug. 23, 2013, 7 pgs.

U.S. Non-Final Office Action, dated Oct. 1, 2014, U.S. Appl. No. 13/524,758, "Digital Rock Analysis Systems and Methods with Multiphase Flow REV Determination," filed Jun. 15, 2012, 13 pgs.

U.S. Non-Final Office Action, dated Mar. 18, 2015, U.S. Appl. No. 13/549,354, "Digital Rock Analysis Systems and Methods with Reliable Multiphase Permeability Determination," filed Jul. 13, 2012, 8 pgs.

Eaton, Timothy T., "On the importance of geological heterogeneity for flow simulation", Eaton, Timothy T., "On the importance of geological heterogeneity for flow simulation," Sedimentary Geology, Dec. 2006, pp. 187-201, School of Earth and Environmental Sciences, New York, 15 pgs.

Fens, Theodoor W., "Petrophysical Properties from small rock samples using Image Analysis techniques", Fens, Theodoor Wouter, "Petrophysical Properties from small rock samples using Image Analysis techniques," 2000, Deift University Press, Deift, the Netherlands, 200 pgs.

Keller, Lukas M. et al., "Pore Space Relevant for Gas Permeability in Opalinus Clay: Statistical Analysis of Homogeneity Percolation (56) References Cited

OTHER PUBLICATIONS and Representative Volume Element", Journal of Geophysical Research: Solid Earth, vol. 118, pp. 1-14, American Geophysical Union: 2013, 14 pgs.

Laroche, C. et al., Laroche C et al: "Two-Phase Flow Properties Prediction from Small-Scale Data Using Pore-Network Modeling", Transport in Porous Media, Kluwer Academic Publishers, DO, vol. • 61, No. 1, Oct. 1, 2885 (2885-18-81), pp. 77-91, XP019268837, ISSN: 1573-1634, 15 pgs.

Liu, et al., "Improved estimates of percolation and anisotropic permeability from 3-D X-ray microtomography using stochastic analyses and visualization", Geochem. Geophys. Geosyst., 10, Q05010, May 29, 2009 (May 29, 2009) [retrieved on Dec. 17, 2013 (Dec. 17, 2013)}., Retried from the Internet:<URL: http://espace.library.curtin.edu.au/cgi-bin/espace.pdf?file=/2010/02/03/file_1/132516> pp. 1-13, 14 pgs.

Wang, Jialu et al., "Porosity characteristics of sandstone by X-ray CT scanning system", Want, Jialu, et al., "Porosity characteristics of sandstone by X-ray CT scanning system," Acta Petrolei Sinica, Nov. 2009, vol. 30, No. 6, PetroChina Exploration and Development Research Institute, Beijing, China, Nov. 2009, 8 pgs.

Culligan, Katherine A. et al., "Interfacial Area Measurements for Unsaturated Flow Through a Porous Medium," Water Resources Research, Dec. 22, 2004, pp. 1-12, vol. 40, W12413, doi:10.1029/2004WR003278.

\* cited by examiner

DIGITAL ROCK ANALYSIS SYSTEMS AND METHODS THAT RELIABLY PREDICT A POROSITY-PERMEABILITY TREND

CROSS-REFERENCE TO RELATED APPLICATIONS

This application claims priority to Provisional U.S. Application Ser. No. 61/692,541, titled "Digital Rock Analysis Systems and Methods that Reliably Predict a Porosity-Permeability Trend" and filed Aug. 23, 2012 by Giuseppe De Prisco, which is incorporated herein by reference.

BACKGROUND

Microscopy offers scientists and engineers a way to gain a better understanding of the materials with which they work. Under high magnification, it becomes evident that many materials (including rock and bone) have a porous microstructure that permits fluid flows. Such fluid flows are often of great interest, e.g., in subterranean hydrocarbon reservoirs. Accordingly, significant efforts have been expended to characterize materials in terms of their flow-related properties including porosity, permeability, and the relation between the two.

Scientists typically characterize materials in the laboratory by applying selected fluids with a range of pressure differentials across the sample. Such tests often require weeks and are fraught with difficulties, including requirements for high temperatures, pressures, and fluid volumes, risks of leakage and equipment failure, and imprecise initial conditions. (Flow-related measurements are generally dependent not only on the applied fluids and pressures, but also on the history of the sample. The experiment should begin with the sample in a native state, but this state is difficult to achieve once the sample has been removed from its original environment.)

Accordingly, industry has turned to digital rock analysis to characterize the flow-related properties of materials in a fast, safe, and repeatable fashion. A digital representation of the material's pore structure is obtained and used to characterize the flow-related properties of the material. However, the size of the digital representation often proves to be an important factor in that a model that is too small will fail to be representative of the physical material, and a model that is too large will consume a disproportionate amount of computational resources with little or no additional benefit. In some cases the size of the model is determined by equipment limitations and it is necessary to make the best of it. It would be desirable to optimize the size of the digital rock model and maximize the amount of information that can be derived from it.

BRIEF DESCRIPTION OF THE DRAWINGS

Accordingly, there are disclosed herein digital rock analysis systems and methods that measure permeability over an extended porosity range. In the drawings.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Figure 1:
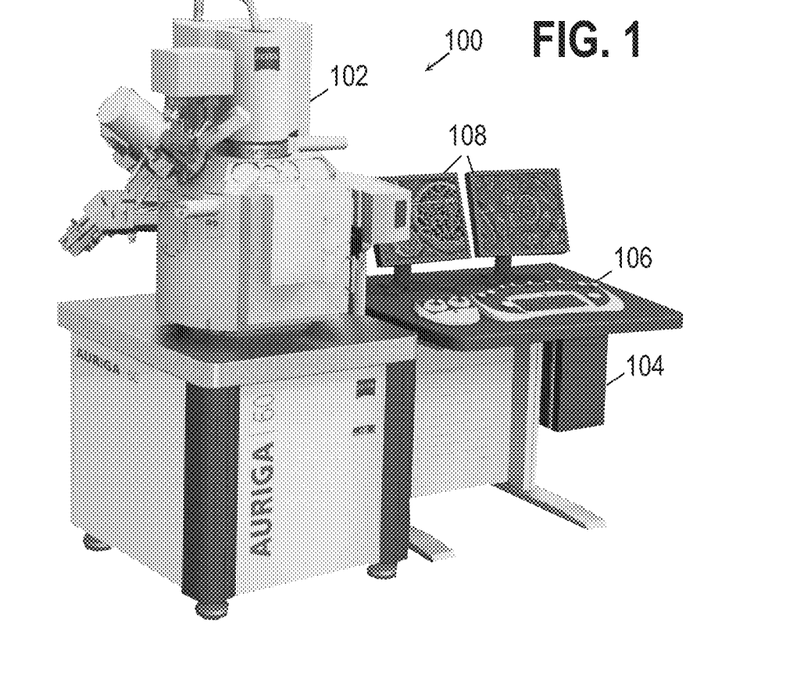
FIG. 1 shows an illustrative high resolution focused ion beam and scanning electron microscope.

For context, FIG. 1 provides an illustration of a high-resolution focused ion beam and scanning electron microscope 100 having an observation chamber 102 in which a sample of material is placed. A computer 104 is coupled to the observation chamber instrumentation to control the measurement process. Software on the computer 104 interacts with a user via a user interface having one or more input devices 106 (such as a keyboard, mouse, joystick, light pen, touchpad, or touchscreen) and one or more output devices 108 (such as a display or printer).

For high resolution imaging, the observation chamber 102 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

The system described above is only one example of the technologies available for imaging a sample. Transmission electron microscopes (TEM) and three-dimensional tomographic x-ray transmission microscopes are two other technologies that can be employed to obtain a digital model of the sample. Regardless of how the images are acquired, the following disclosure applies so long as the resolution is sufficient to reveal the porosity structure of the sample.

The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present disclosure.

Figure 2:
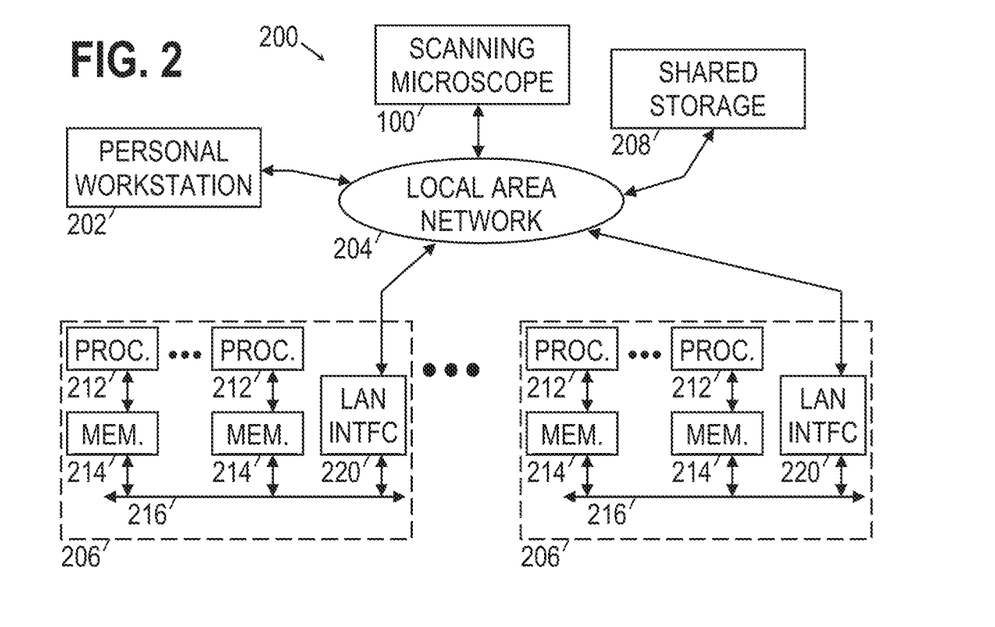
FIG. 2 shows an illustrative high performance computing network.

FIG. 2 is an example of a larger system 200 within which the scanning microscope 100 can be employed. In the larger system 200, a personal workstation 202 is coupled to the scanning microscope 100 by a local area network (LAN) 204. The LAN 204 further enables intercommunication between the scanning microscope 100, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the scanning microscope. For tasks having small computational demands, the software may be executed on the personal workstation 202, whereas computationally demanding tasks may be preferentially run on the high performance computing platform 206.

Figure 3A:
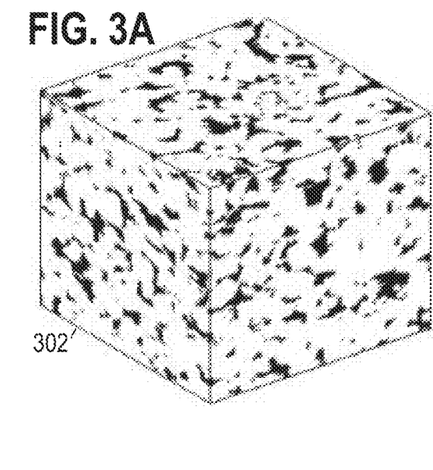
FIG. 3A shows an illustrative volumetric representation of a sample.

FIG. 3A is an illustrative image 302 that might be acquired by the scanning microscope 100. This three-dimensional image is made up of three-dimensional volume elements ("voxels") each having a value indicative of the composition of the sample at that point.

Figure 3B:
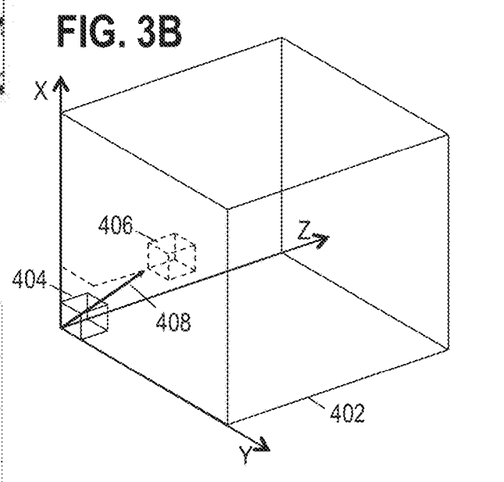
FIG. 3B shows an illustrative coordinate system for performing sample analysis.
Figure 4:
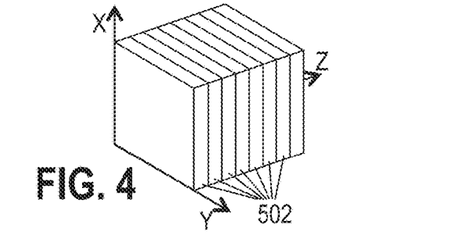
FIG. 4 shows an illustrative division of a model region into slices.

FIG. 3B provides a coordinate system for a data volume 402, with the x-, y-, and z-axes intersecting at one corner of the volume. Within the data volume, a subvolume 404 is defined. The illustrated subvolume 404 is a cube having sides of length a, but other subvolume shapes may alternatively be used, e.g., a parallelogram having the same shape as the overall data volume, a sphere, or a tetrahedron. It is desirable, though not necessary, for the chosen subvolume shape to be scalable via a characteristic dimension such as diameter or an edge length. The subvolume 404 can be defined at any position 406 within the data volume 402 using a displacement vector 408 from the origin to a fixed point on the subvolume. Similarly, sub-subvolumes can be defined and positioned within each subvolume. For example, FIG. 4 shows a subvolume divided into slices 502 perpendicular to the flow direction (in this case, the z-axis).

Figure 5A:
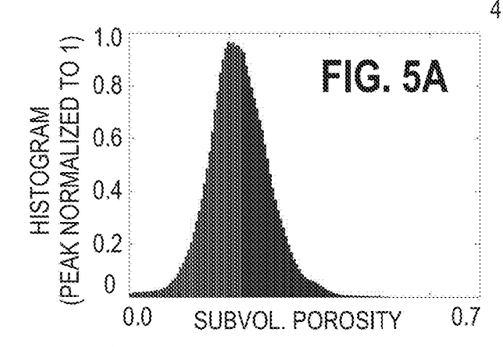
FIG. 5A shows an illustrative distribution of subvolume porosity.

One way to characterize the porosity structure of a sample is to determine an overall parameter value, e.g., porosity. The image is processed to categorize each voxel as representing a pore or a portion of the matrix, thereby obtaining a pore/matrix model in which each voxel is represented by a single bit indicating whether the model at that point is matrix material or pore space. The total porosity of the sample can then be determined with a straightforward counting procedure. Following the local porosity theory set forth by Hilfer, ("Transport and relaxation phenomena in porous media" Advances in Chemical Physics, XCII, pp 299-424, 1996, and Biswal, Manwarth and Hilfer "Three-dimensional local porosity analysis of porous media" Physica A, 255, pp 221-241, 1998), when given a subvolume size, the porosity of each possible subvolume in the model may be determined and shown in the form of a histogram (see, e.g., FIG. 5A). Note that the distribution will vary based on subvolume size. While helpful, the distribution of FIG. 5A reveals only a limited amount of information about the heterogeneity of the model and does not account for directional anisotropy of the sample.

Figure 5B:
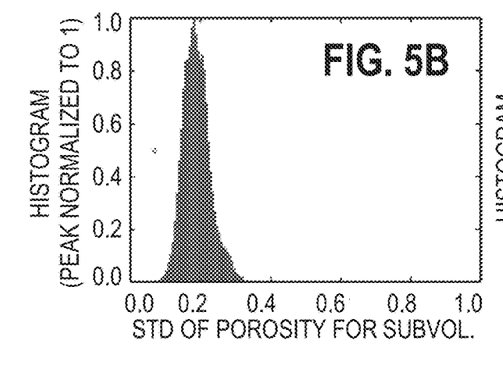
FIGS. 5B-5C show illustrative distributions of porosity-related parameter variation.

One example of a more sophisticated measure is the standard deviation of porosity along a specific direction. As shown in FIG. 4, a volume (or subvolume) can be divided into slices perpendicular to the flow direction. The structure of the pores may cause the porosity to vary from slice to slice, from which a standard deviation of porosity along the flow direction can be determined. While this measure itself provides a useful indication of the pore structure, it can be extended. If the sample volume is divided into subvolumes (see, e.g., FIG. 3B) and the standard deviation of porosity measured (relative to the average porosity of the whole sample and normalized by that same averaged porosity) for each subvolume, it yields a histogram such as that shown in FIG. 5B. Again, this histogram is a function of the subvolume size. As the subvolume size grows from near zero to the size of a representative elementary volume ("REV"), the histogram converges and becomes nearly Gaussian in shape. (By way of comparison, when the subvolume dimension in a perfectly periodic "ideal" sample has a size that is an integer multiple of the REV size, the histogram is going to have zero mean and zero variance, in other words a Dirac delta function centered at zero.)

The REV size depends on the statistical measure used to define it. The foregoing approach yields an REV suitable for Darcian analysis, and hence the REV size (e.g., diameter, length, or other dimension) is referred to herein as the "integral scale" or "Darcian scale". Other length scales may also be important to the analysis. For example, the percolation scale, defined here as the subvolume size at which the average difference between total porosity and the connected porosity (porosity connected in some fashion to the inlet face) falls below a threshold, for example without limitation: 1%. This difference is also termed "disconnected porosity", and depending on the specific context, may be limited to as little as 1% or as much as 10%, though the upper limit is preferably no more than 2%. Other threshold values may also be suitable, and it is believed that other definitions of percolation length would also be suitable. See, e.g., Hilfer, R. (2002), "Review on scale dependent characterization of the microstructure of porous media", Transp. Porous Media, 46, 373-390, doi:10.1023/A:1015014302642. We note that the percolation scale can be larger than, or smaller than, the integral scale, so generally speaking the larger of the two should be used to define a truly representative elementary volume.

Another measure of porosity structure is the standard deviation of surface-to-volume ratio. If the surface area (or in a two-dimensional image, the perimeter) of the pores in each slice 502 (FIG. 4) is divided by the volume (or in 2D, the surface area) of the corresponding pores, the resulting ratio exhibits some variation from slice to slice, which can be measured in terms of the standard deviation. As the standard deviation of the surface-to-volume ratio is determined for each subvolume in a model, a histogram such as that in FIG. 5B results. As before, the histogram should converge and approximate a Gaussian distribution when the subvolume size reaches or exceeds the integral scale.

Figure 6:
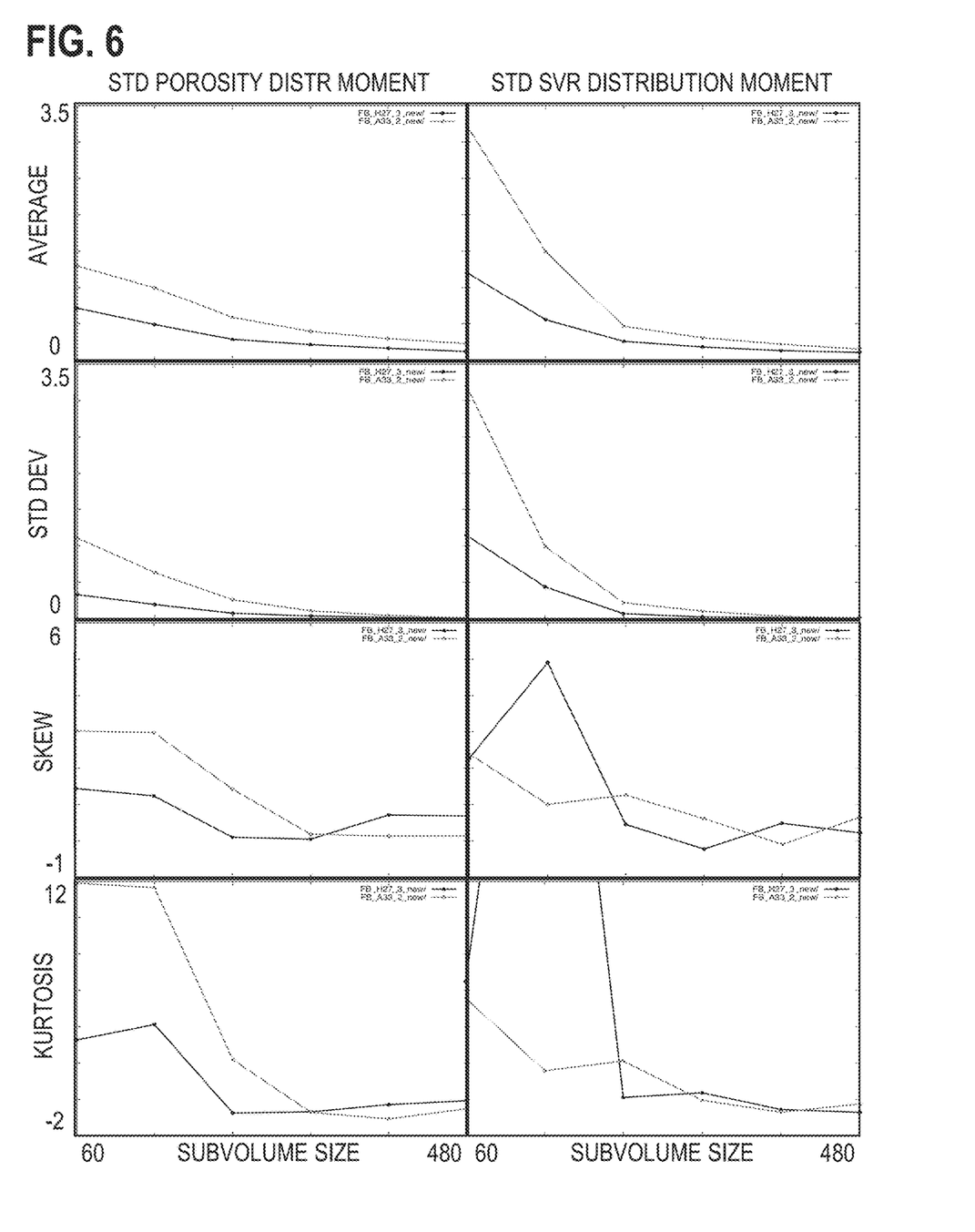
FIG. 6 illustrates a dependence of distribution moments on subvolume size.

FIG. 6 compares the moments of both histograms (standard deviation of porosity and standard deviation of surface-to-volume ratio (SVR)) for two different samples as a function of subvolume size. The first four moments (mean, standard deviation, skew, and kurtosis) are shown for subvolumes sizes as measured by edge length of the subvolume (which is a cube) in the range from 60 to 480 units. The first moment for both samples approaches zero, i.e., the center of the standard deviation of porosity and SVR distributions approaches a zero variation with respect to the porosity and SVR of the whole sample, meaning that on average the subvolumes have the same porosity and SVR as the whole sample when the subvolume size reaches about 200 units. The second moment for both samples becomes similarly close to zero at this length scale (200), i.e., the probability of a subvolume having the same standard deviation of porosity and SVR as the whole sample is quite high. The asymmetry of the distribution (as indicated by the skew value) and the kurtosis also become small at and above this threshold, suggesting that the REV size, to define an integral length scale according to Darcy analysis, is no larger than 200 units. As explained in U.S. Provisional Application 61/618,265 titled "An efficient method for selecting representative elementary volume in digital representations of porous media" and filed Mar. 30, 2012 by inventors Giuseppe De Prisco and Jonas Toelke (and continuing applications thereof), either or both of these measures can be employed to determine whether reduced-size portions of the original data volume adequately represent the whole for porosity- and permeability-related analyses.

Various methods for determining permeability from a pore/matrix model are set forth in the literature including that of Papatzacos "Cellular Automation Model for Fluid Flow in Porous Media", Complex Systems 3 (1989) 383-405. Any of these permeability measurement methods can be employed in the current process to determine a permeability value for a given subvolume.

As mentioned in the background, the size of the model may be constrained by various factors including physical sample size, the microscope's field of view, or simply by what has been made available by another party. It may be that a model is subjected to the foregoing analysis and shown to have an integral scale and/or a percolation scale that is substantially same as the size of the model. In such a case, the size of the representative elementary volume should be set based on the larger of the integral scale or the percolation scale, and there are a sharply limited number of subvolumes in the model having this size.

Figure 7A:
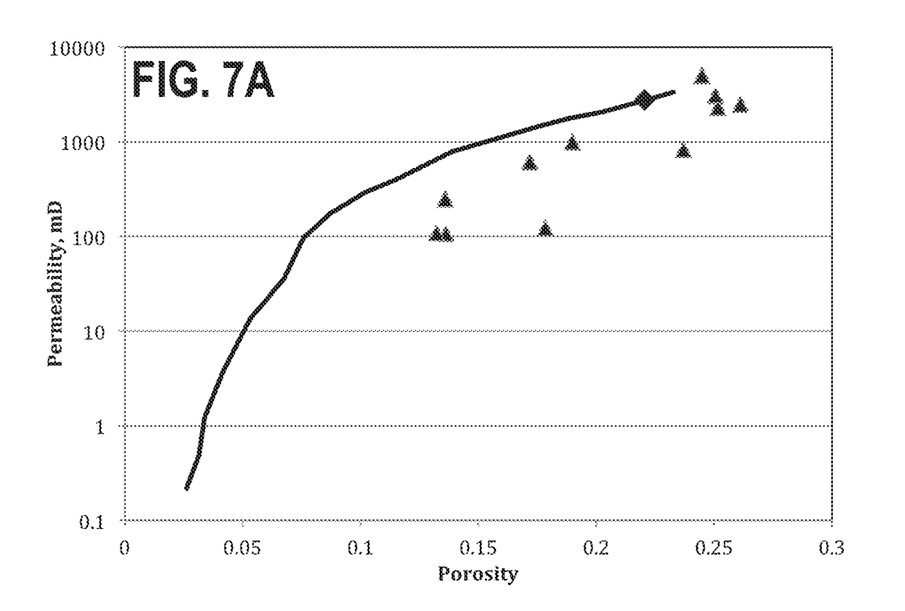
FIG. 7A shows an illustrative porosity-permeability trend derived using a randomly-positioned sub-Darcian subvolume.

FIG. 7A is a graph of permeability (on a logarithmic scale) as a function of porosity for a sample of Fountain Blue rock. The solid curve is derived from the published literature on this rock facies and is shown here solely for comparative purposes. It is desired to apply the disclosed methods to samples for which this curve may be unknown, so that the curve can be determined or at least estimated. Alternatively, the disclosed methods may be employed to verify that the sample actually exhibits the expected relationship.

The size of the whole sample in this case is larger than the REV size. When taken as a whole, the model yields only one permeability vs. porosity data point which appears in FIG. 7A as a diamond. The diamond is on the curve, indicating that the measurement is accurate. Due to the limited amount of information this single point provides, it is desired to extend the range of data points insofar as it is possible with the given model, so as to predict the permeability values for different hypothetical members of this rock family having larger or smaller porosities.

One solution is to employ REV-sized subvolumes and independent measure their porosity-permeability values. This approach is only feasible if the whole sample is much larger than the REV size. This is often not the case, so the measured porosity-permeability values are likely to be limited to a very small range close the measurement for the sample as a whole.

Since the model exhibits a range of subvolume porosities (see, e.g., FIG. 5A) that increases as the subvolume size shrinks, the user may be tempted to reduce the subvolume size below the REV size, making a greater number of subvolume positions available for exploring the poro-perm trend, each subvolume potentially yielding a different porosity-permeability measurement. The triangles in FIG. 7A show the resulting measurements from a randomly-chosen set of subvolume positions, with the subvolume having an edge length of about half that of the REV. Notably, these data points suggest a substantially incorrect relationship between porosity and permeability. Hence, a random-choice strategy appears destined to fail.

Figure 7B:
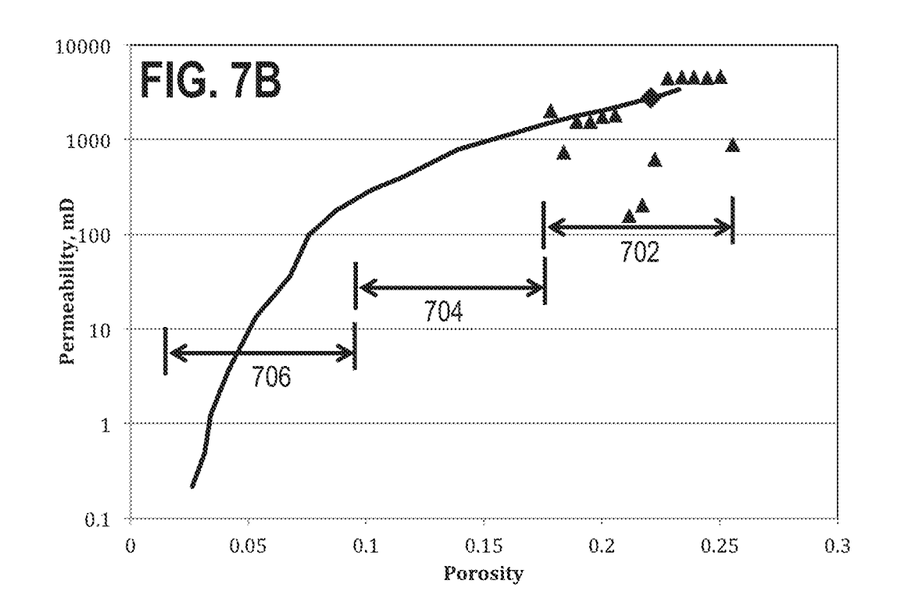
FIG. 7B shows the illustrative porosity-permeability trend derived by positioning the subvolume with conditional probability.

Accordingly, we propose a strategy using reduced-size subvolumes with conditionally-selected positions rather than randomly chosen positions. FIG. 7B is a graph similar to FIG. 7A, but this time with conditionally-chosen subvolume positions as provided further below. Note that the substantial majority of measurements are now aligned with the solid curve, indicating that it is possible to extract a porosity-permeability relationship over an extended porosity range even when using a subvolume size below the REV size. The porosity ranges 702, 704, and 706 are referenced further below, but we note here that 702 indicates the porosity range that is reachable in this sample with a subvolume dimension about half that of the REV size, variation below a threshold of 40% of the mode of the standard deviation of porosity distribution, and disconnected porosity of no more than 1% of the subvolume's total porosity. Porosity range 704 indicates the region where the average disconnected porosity lies between 1% and 10%, and porosity range 706 indicates the region where the average disconnected porosity is on the order of 20%.

Figure 8:
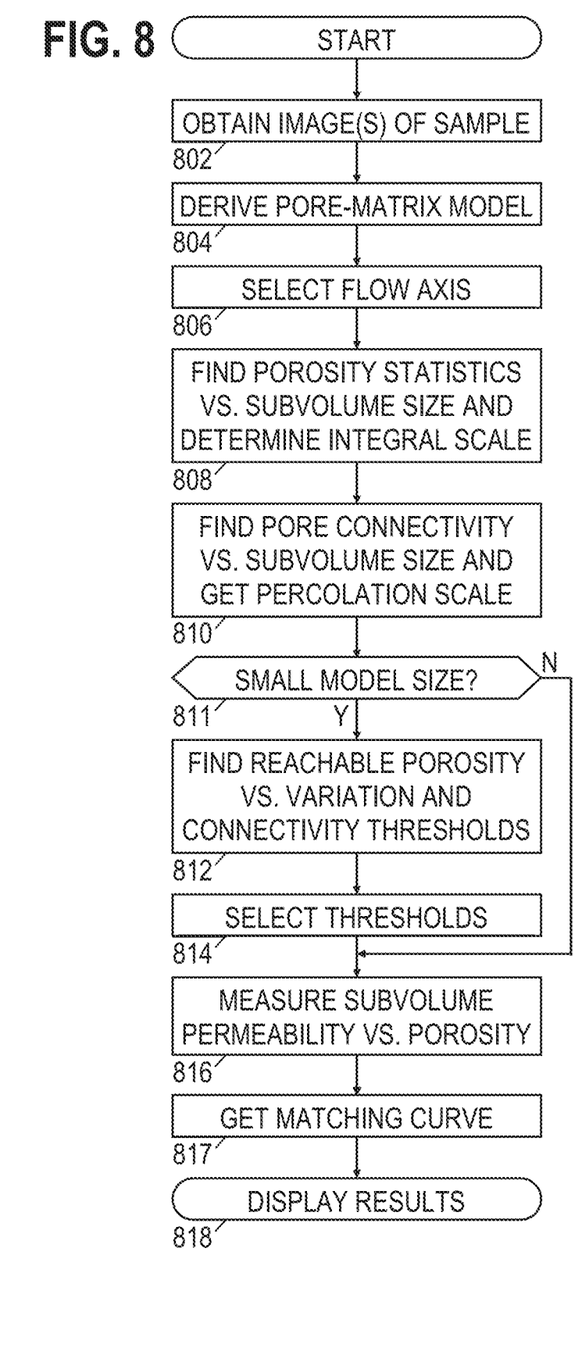
FIG. 8 is a flowchart of an illustrative analysis method.

Given the foregoing principles and practices, we turn now to a discussion of certain methods that enable determination of a porosity-permeability relationship over an extended porosity range when analyzing a small digital rock model. FIG. 8 is an illustrative flowchart to support this discussion.

The illustrative workflow begins in block 802, where the system obtains one or more images of the sample, e.g., with a scanning microscope or tomographic x-ray transmission microscope. Of course the images can be alternatively supplied as data files on an information storage medium. In block 804, the system processes the images to derive a pore/matrix model. Such processing can involve sophisticated filtering as set forth in existing literature to classify each image voxel as representing a pore or a portion of the matrix.

In block 806, the system determines a flow axis. This determination may be based on external factors (e.g., the orientation of the material sample relative to the well, formation pressure gradients, client specifications). When the axis is not based on external factors, it may be selected based on an analysis of the pore/matrix model (e.g., choosing the axis with the highest absolute permeability, or the axis having the lowest standard deviation of porosity).

Figure 5C:
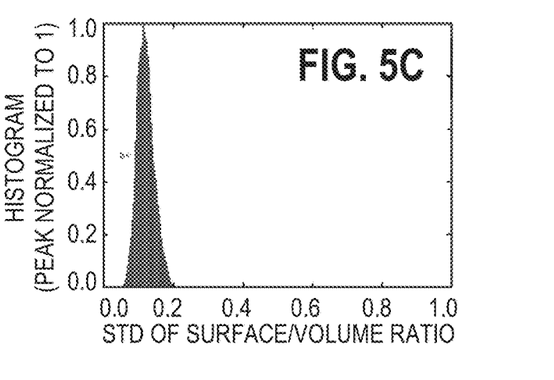

In block 808, the system finds the distributions of standard deviation of porosity (e.g., FIG. 5B) at different subvolume sizes, distributions of standard deviation of surface to volume ratio (e.g., FIG. 5C), and/or other distributions of porosity-related parameter variation as a function of subvolume size. From these distributions, the system determines a (Darcian) integral scale. Note that for a useful porosity-permeability trend to be extractable, we believe that the dimensions of the original model should be at least four or five times the dimensions of the REV.

In block 810, the system finds a measure of pore connectivity at different subvolume sizes. The connectivity can be characterized in a variety of ways, including finding a percentage or normalized volume of the subvolume pore space connected to an inlet face of the pore/matrix model. In accordance with the Hilfer's Local Porosity theory, a histogram of the subvolume connectivities will exhibit a mean and a mode, either of which could be used as a connectivity measure. As an alternative, the percentage difference between the total subvolume pore space and the subvolume pore space connected to an inlet face (hereafter termed the disconnected pore percentage) can be used. From the relationship between the connectivity measure and subvolume size, the system determines a percolation scale, e.g., as one step above the largest subvolume size with a disconnected pore percentage below a threshold.

In block 811, the system determines whether the whole model size is substantially (four or five times) bigger than the larger of the percolation scale or the integral scale. If the model is substantially bigger than the larger of these scales, an adequate porosity range should be reachable using a subvolume size equal to the larger of these two scales. Hence the system proceeds with a systematic (potentially a pseudo-random), unconditional selection of subvolumes and in block 816 determines the porosity-permeability value associated with each subvolume. A plot of these data points, with an optional matching curve determined in block 817, should reveal the porosity-permeability relationship for the sample.

Otherwise, when the whole model size is approximately the same as the larger of the percolation or integral scales, it is desirable to derive this relationship using smaller (sub-REV) subvolumes. (This might not be possible if the larger of the two scales is the percolation scale.) In block 812, the system determines a reachable porosity, either for a given subvolume size or for each of multiple subvolume sizes. As previously mentioned, for a given size, each subvolume position yields a different potential measurement on the porosity-permeability space. However, when operating in the sub-REV domain, not all subvolumes are used to extract the poro-perm trend. Rather, the system performs a conditional probability analysis, placing one or more conditions on which subvolumes can be employed in this analysis. One condition is that the standard deviation of porosity of the subvolume should not vary too much from the standard deviation of porosity of the full model. Accordingly, the system requires that the subvolume have a standard deviation of porosity below a given threshold (hereafter termed the "variation threshold"). In one embodiment, this threshold is set at the $20^{th}$ percentile, meaning that the subvolume should have a standard deviation in the bottom fifth of the distribution (in FIG. 5B, this would be below about 0.16). In another embodiment, the variation threshold is set at the $40^{th}$ percentile (about 0.19 in FIG. 5B). Some system embodiments may employ a similar threshold on the standard deviation of SVR as an additional or alternative condition.

Another condition that may be imposed by the system is that the subvolume have only a disconnected porosity that is below a given threshold (hereafter termed the "connectivity threshold"). In one embodiment, the system requires that the subvolume have no more than 1% disconnected porosity. In another embodiment, the system allows up to 2% disconnected porosity. In a preferred system embodiment, the subvolume must be below both the variation threshold and the connectivity threshold. The range of porosities possessed by subvolumes satisfying these conditions is the "reachable porosity". In FIG. 7B, range 702 is the reachable porosity for subvolumes having an edge size of about 50% of the REV below the $40^{th}$ percentile threshold with no more than 1% disconnected porosity. The system optionally adjusts the thresholds to determine the effect on the reachable porosity range and the data point scatter. For example, it may be the case that only a small sacrifice in range is made by reducing the connectivity threshold from 10% to 4%, but a significant reduction in scatter may be achievable by this reduction. Conversely, the system may determine that a variation threshold of the $20^{th}$ percentile yields an insufficient range of reachable porosity and accordingly increases the variation threshold to the $40^{th}$ percentile to achieve the desired range. The system may vary the thresholds to extract this information, and in block 814 select the threshold values that yield the best results (i.e., maximum reachable porosity that still yields with acceptable data scatter).

In block 816, the system determines the porosity-permeability measurements for the selected subvolumes satisfying the screening conditions. In block 817, the system optionally fits a curve to the data points and/or provides a comparison curve derived from the literature. The resulting relationship can then be displayed to a user, e.g., in a form similar to FIG. 7B.

For explanatory purposes, the operations of the foregoing method have been described as occurring in an ordered, sequential manner, but it should be understood that at least some of the operations can occur in a different order, in parallel, and/or in an asynchronous manner.

Numerous variations and modifications will become apparent to those skilled in the art once the above disclosure is fully appreciated. For example, the foregoing disclosure describes illustrative statistics for determining an REV size, but other suitable statistics exist and can be employed. It is intended that the following claims be interpreted to embrace all such variations and modifications.

What is claimed is:

1. A method that comprises:
   scanning a sample using an electron microscope to obtain an image of the sample;
   processing the image to derive a three-dimensional pore/matrix model;
   measuring, by a processor, a distribution of porosity-related parameter variation for the pore/matrix model as a function of subvolume size;
   measuring, by the processor, a pore connectivity-related parameter for the pore/matrix model as a function of subvolume size;
   determining, by a processor, a reachable porosity for subvolumes in the model where the distribution of porosity-related parameter variation of the subvolumes is below a variation threshold and the pore connectivity-related parameter of the subvolumes is below a connectivity threshold;
   adjusting, by the processor, either or both of the variation threshold or the connectivity threshold to determine the subvolumes offering a maximum reachable porosity;
   determining, by the processor, porosity and permeability values associated with the determined subvolumes; and
   displaying said permeability values as a function of porosity.

2. The method of claim 1, further comprising determining an integral scale based at least in part on said distribution of porosity-related parameter variation as a function of subvolume size.

3. The method of claim 2, further comprising determining a percolation scale based at least in part on the connectivity-related parameter as a function of subvolume size.

4. The method of claim 1, further comprising determining, by the processor, porosities possessed by the subvolumes and selecting, by the processor, a subvolume size offering a maximum reachable porosity range from the determined porosities by determining that at least one of an integral scale or a percolation scale are to the same size as a dimension of the pore/matrix model.

5. The method of claim 1, wherein the sample is a physical rock sample.

6. The method of claim 1, wherein measuring the distribution of porosity-related parameter variation for the pore/matrix model as a function of the size of the subvolume further comprises wherein the porosity-related parameter variation comprises a standard deviation of porosity of slices of the subvolume and the slices are divided perpendicular to a flow direction of the subvolumes.

7. The method of claim 6, further comprising measuring a distribution of standard deviation of pore surface to volume ratio.

8. The method of claim 1, wherein said determining a reachable porosity for subvolumes includes:
screening out subvolumes having porosity-related parameter variation above the variation threshold;
screening out subvolumes having a connectivity-related parameter value above the connectivity threshold.

9. The method of claim 8, wherein the variation threshold screens subvolumes having variation in an upper ⅗ths of the distribution.

10. The method of claim 8, wherein the connectivity threshold screens subvolumes having more than 10% disconnected porosity.

11. A system for analyzing a sample, comprising:
an electron microscope operable to produce an image of the sample;
a memory having software; and
one or more processors coupled to the memory to execute the software, the software causing the one or more processors to:
derive a three-dimensional pore/matrix model from the image;
measure a distribution of porosity-related parameter variation for the pore/matrix model as a function of subvolume size;
measure a pore connectivity-related parameter for the pore/matrix model as a function of subvolume size;
determining a reachable porosity for subvolumes in the model where the distribution of porosity-related parameter variation of the subvolumes is below a variation threshold and the pore connectivity-related parameter of the subvolumes is below a connectivity threshold;
adjusting either or both of the variation threshold or the connectivity threshold to determine the subvolumes offering a maximum reachable porosity; and
determining porosity and permeability values associated with the determined subvolumes.

12. The system of claim 11, wherein the software further causes the one or more processors to determine an integral scale based at least in part on said distribution of porosity-related parameter variation as a function of subvolume size.

13. The system of claim 12, wherein the software further causes the one or more processors to determine a percolation scale based at least in part on the connectivity-related parameter as a function of subvolume size.

14. The system of claim 11, further comprising determining, by the processor, porosities possessed by the subvolumes and selecting a subvolume size offering a maximum reachable porosity range from the determined porosities by determining that at least one of an integral scale or a percolation scale are the same size to a dimension of the pore/matrix model.

15. The system of claim 11, wherein the sample is a physical rock sample.

16. The system of claim 11, wherein the distribution of porosity-related parameter variation is a distribution of standard deviation of porosity.

17. The system of claim 16, wherein the software further causes the one or more processors to measure a distribution of standard deviation of pore surface to volume ratio.

18. The system of claim 11, wherein as part of said determining a reachable porosity for subvolumes, the software causes the one or more processors to:
screen out subvolumes having porosity-related parameter variation above a given variation threshold;
screen out subvolumes having a connectivity-related parameter value above a given connectivity threshold.

19. The system of claim 18, wherein the variation threshold screens subvolumes having variation in an upper ⅗ths of the distribution.

20. The system of claim 18, wherein the connectivity threshold screens subvolumes having more than 10% disconnected porosity.

* * * * *